(12) United States Patent
Becker et al.

(10) Patent No.: US 6,868,710 B2
(45) Date of Patent: Mar. 22, 2005

(54) PINCH GRIP DYNAMOMETER FIELD TESTING CALIBRATION STAND

(76) Inventors: Theodore J. Becker, 5213 23rd Ave. West, Everett, WA (US) 98203; Massimo J. Becker, 5213 23rd Ave. West, Everett, WA (US) 98203

( * ) Notice: Subject to any disclaimer, the term of this patent is extended or adjusted under 35 U.S.C. 154(b) by 94 days.

(21) Appl. No.: 10/351,553

(22) Filed: Jan. 27, 2003

(65) Prior Publication Data

US 2004/0144156 A1 Jul. 29, 2004

(51) Int. Cl.$^7$ ............................................. G01L 25/00
(52) U.S. Cl. ........................................ 73/1.08; 73/1.15
(58) Field of Search ........................ 73/379.02–379.03, 73/1.08, 1.13, 1.15; 600/587, 595

(56) References Cited

U.S. PATENT DOCUMENTS

| | | | |
|---|---|---|---|
| 2,140,331 A | * 12/1938 | Rabkin .................... | 73/1.08 X |
| 2,321,652 A | 6/1943 | Carliss ..................... | 73/1.08 |
| 2,672,755 A | 2/1954 | Hohner .................... | 73/1.08 X |
| 3,585,840 A | 6/1971 | Landsness ................. | 73/1.08 |
| 3,995,471 A | 12/1976 | Konomi et al. ............ | 73/1.14 |
| 4,090,393 A | 5/1978 | Kharitonov et al. ........ | 73/1.08 |
| 4,467,815 A | * 8/1984 | O'Brien et al. ............ | 600/553 |
| 4,766,758 A | * 8/1988 | Lucas et al. ............ | 73/862.045 |
| 4,798,094 A | 1/1989 | Newhall et al. ........ | 73/1.08 X |
| 5,020,357 A | 6/1991 | Kovacevic et al. .......... | 73/1.15 |
| RE35,598 E | * 9/1997 | Sadoff et al. ......... | 73/379.02 X |
| 5,945,590 A | 8/1999 | Becker ..................... | 73/1.13 |
| 6,673,026 B2 | * 1/2004 | Pozos et al. ................ | 600/587 |

FOREIGN PATENT DOCUMENTS

| | | | | |
|---|---|---|---|---|
| EP | 937974 A2 | * | 8/1999 | ........... G01L/25/00 |
| JP | 09079931 A | * | 3/1997 | ........... G01L/25/00 |

OTHER PUBLICATIONS

Flood–Joy, Maureen, Mathiowetz, Virgil,; "Grip–Strength Measurement: A Comparison of Three Jamar Dynamometers"; 1995, pp. 235–243. (The Occupational Therapy Journal of Research 7:4), month not given.

Fess, Elaine Ewing, "The Need for Reliability and Validity in Hand Assessment Instruments", Sep. 1986, pp. 621–623. (The Journal of Hand Surgery, vol. 11A, No. 5).

Radwin, R.G., "A Linear Force–summing Hand Dynamometer Independent of Point of Application", Oct. 1991, pp. 339–340. (Applied Ergonomics 1991, 22.5).

Harkonen, Riita et al., "Accuracy of the Jamar Dynamometer", Oct. 1993, 259–262. (Journal of Hand Therapy).

D. Schapmire, MS, JD et al., "Simultaneous Bilateral Testing: Validation of a New Protocol to Detect Insincere Effort During Strength Testing", Jul./Sep. 2002, pp. 242–250, (Journal of Hand Therapy).

Sales phamlet from Sammons Preston AbilityOne Corporation, copyright 1999, month not given, pp. 1–9 & 3½ sheets.

Ev Innes et al., "Reliability of Work–Related Assessments", 1999, pp. 107–124, (Work 13), month not given.

Elaine Fess, "A Method for Checking Jamar Dynamometer Calibration", Oct.–Dec. 1987, pp. 28–32, (Journal of Hand Therapy).

* cited by examiner

Primary Examiner—Thomas P. Noland
(74) Attorney, Agent, or Firm—Richard C. Litman (57) ABSTRACT

A pinch grip dynamometer field testing calibration stand for a pinch or finger grip dynamometer having a base defined by a platform and a vertical post, a dynamometer holder attached to the platform, and upper and lower calibration plates slidable on the post. The dynamometer is supported by the holder with its load application point (a concave groove in the case of a mechanical dynamometer, or the concave face of a button in the case of a hydraulic dynamometer) in proximity to the post. The bottom surface of the lower calibration plate has a convex protrusion which applies a load to the dynamometer. The load is supplied by calibrated weights of known mass supported in a groove on the top surface of the lower calibration plate, and by a groove in the bottom surface of the upper calibration plate when the weight needs support for its upper portion.

11 Claims, 10 Drawing Sheets

PINCH GRIP DYNAMOMETER FIELD TESTING CALIBRATION STAND

BACKGROUND OF THE INVENTION

1. Field of the Invention

The present invention relates generally to medical devices for measuring grip strength, and particularly to a pinch grip dynamometer field testing calibration stand for calibrating a pinch grip dynamometer in the field without having to return the dynamometer to the factory for testing.

2. Description of the Related Art

Various portable dynamometers have been devised for determining the effects or application of loads in impact studies and medical applications, and particularly for determining grip strength, over the past few years. One of the most important problems of the conventional dynamometers is that they are lightweight and easy to move from place to place, which can cause them to become inaccurate due to mechanical jarring during transport. Also, in 1994 and 1995, the American Medical Association adopted a formula for hand injury percentage of impairment using a hand-held hand and finger grip dynamometers. Practitioners using the devices are expected to document that their use of the dynamometers is accurate. Once the dynamometer has left the manufacturing facility, it is presumed by industry, government agencies and small business consumers that necessary calibrations have been accurately determined and that the dynamometer will give correspondingly accurate comparative results in the field during the lifetime of the dynamometer.

However, testing by an independent source, such as a local Government Department of Weights and Measures, has advised that no device has been available to permit a practitioner to independently verify the accuracy of conventional dynamometers through a load bearing test as described herein. In the related art of calibration of hand grip dynamometers for measuring hand grip strength, generally the manufacturer of the hand grip dynamometer provides recalibration and other cleaning services to owners and practitioners, but this requires that owners and practitioners ship the dynamometer to the manufacture, as shown by sales pamphlets from Sammons Preston. However, this process means that the dynamometer is out of service for the periods involved in shipping and testing the instruments.

In the field of hand grip dynamometers, U.S. Pat. No. 5,945,590, issued on Aug. 31, 1999 to Theodore Becker, a co-inventor of the present invention, provides a portable and convenient stand to calibrate a hand grip dynamometer which tightly holds the hand grip of the hand grip dynamometer while applying weights to a plate that pushes down the hand grip. This '590 device provides a specialized location of load bearing that is different from the calibration stand for pinch grip dynamometers according to the present invention. The device described in the '590 patent uses a fixture shape which is unique to the hand grip dynamometer, but which is not appropriate for the pinch grip dynamometer. The '590 device, therefore, has unique stabilization location and a unique pressure location. The hand grip dynamometer has a different force receiving surface for the hand or all fingers of the hand rather than the fingers. The hand grip dynamometer has two load bearing points to be accommodated by its calibration stand, as compared to the single load bearing point of the finger grip dynamometer, which therefore requires a different calibration stand.

Other calibration devices have been developed for testing various devices. For example, U.S. Pat. No. 2,672,755, issued on February 1954 to Hohner, discloses a measuring device for forces, and more particularly, a calibrating attachment for indicating the limits of a predetermined tolerance on the scale of the measuring device. Although the mechanism for calibration is included as part of the measuring device, the test loads are applied at one end of a pivoted lever, a feature absent from the present invention.

U.S. Pat. No. 5,020,357, issued on Jun. 4, 1991 to Kovacevic et al., discloses a calibration stand for multi-force sensors which is capable of providing six components of force and moment to the sensors using support and loading apparatus on the calibration stand. Although the stand is a compact portable unit, it provides for holding the sensor in a precise position by fully permitting pitch and lateral adjustments for axial and roll or moment loading. By contrast, the portable and compact dynamometer calibration stand of the present invention does not need to provide for any lateral adjustment for axial and roll or moment loading. Also, the present invention uses simple masses or weights for calibration, whereas Kovacevic et al. uses electronic load cells.

U.S. Pat. No. 2,321,652, issued to Carliss in June, 1943, discloses a dynamometer which resembles an old-fashioned weighing machine. Weights or forces are determined by a mechanical weighing scale which is interconnected to an analog lever arm by a spring loaded mechanical linkage for indicating a force reading via a graduated scale. The mechanical linkage is quite involved, including a series of gears for transmitting various applied forces. U.S. Pat. No. 3,585,840, issued to Landsness in June, 1971, discloses a force generator which generates a force of constant amplitude and changing direction for calibrating force-sensing instruments. A resilient rod with a bearing surface provided on the free end of the rod is anchored to the instrument to be calibrated in a cantilevered arrangement. With this design, the load capacity is limited due to moments generated by the applied force and exerted on the rod. Beyond a critical applied force, failure could occur in the rod in the form of fracture, bending, etc.

U.S. Pat. No. 3,995,471, issued to Konomi et al. in December, 1976, discloses a device for calibrating a chassis dynamometer comprising a drive wheel for driving rollers of the dynamometer. The drive wheel is carried by a frame via a spring. A fluid pressure operated jack selectively lifts up the drive wheel to disengage it from rollers. U.S. Pat. No. 4,090,393, issued to Kharitonov et al. on May 1978, discloses a method and apparatus for calibrating a dynamometer wherein a force of gradual magnitudes is applied to two separate cross beams. A checking or calibrating crossbeam houses a weight which is compared to a master crossbeam upon which forces of gradual magnitudes are placed for calibration.

U.S. Pat. No. 4,798,094, issued to Newhall et al. in January, 1989 discloses an apparatus having hydrostatic bearings which provide centering of a piston and alignment of the piston-to-cylinder interface.

Several recent journal articles suggest the need in the art for reliable calibration of grip strength dynamometers, including: "Grip-Strength Measurement: A Comparison of Three Jamar Dynamometers", Flood-Joy et al., *The Occupational Therapy Journal of Research*, 7:4 (1995); "The Need for Reliability and Validity in Hand Assessment Instruments", E. E. Fess, *The Journal of Hand Surgery*, Vol. 11A, Number 5 (1986); "A Linear Force-summing Hand Dynamometer Independent of Point Application", Radwin et al., *Applied Ergonomics* (1991); "Simultaneous Bilateral Testing: Validation of a New Protocol to Detect Insincere Effort During Strength Testing", D. Schapmire et al., *Journal of Hand Therapy* (2002); "Reliability of Work Related Assessments", Ev Innes et al., *Work*, Vol. 13 (1999); "A Method for Checking Jamar Dynamometer Calibration", E. Fess, *Journal of hand Therapy* (1987); and "Accuracy of the Jamar Dynamometer", Harkonen et al. (1993).

The calibration stand to field test pinch or finger grip dynamometers according to the instant invention is different from the prior and related art, in that it provides automatic calibration via load testing for a pinch grip dynamometer with reduced material elements and uncomplicated structure. This significantly improves portability of the device. No portable device or device available to the practitioner has been made for calibrating the finger or pinch grip dynamometer in the field.

None of the above inventions and patents, taken either singly or in combination, is seen to describe the instant invention as claimed. Thus a pinch grip dynamometer field testing calibration stand solving the aforementioned problems is desired.

SUMMARY OF THE INVENTION

The present invention is a calibration testing stand for a pinch or finger grip dynamometer for field use. The stand has a base including a platform and a post mounted on the platform. The stand has a dynamometer holder mounted on the platform for securing a pinch grip dynamometer for testing, and upper and lower calibration plates. The holder has a recession defined therein for receiving the dynamometer, and set screws for securing the dynamometer to the holder at a fixed distance from the post. The lower calibration plate has a contact protrusion extending from its lower surface adapted for snugly fitting the load application point on the dynamometer, and an upper surface having a groove defined therein for receiving a calibration weight. The dynamometer is calibrated by securing the dynamometer in the holder, lowering the lower calibration plate onto the load application point to tare the device and placing a calibration weight in the groove. For larger calibration weights the upper calibration plate has a groove in its lower surface for supporting the calibration weight between the upper and lower plates.

The pinch grip dynamometer field testing calibration stand of the present invention may be used with different types of pinch grip dynamometers. One form of pinch grip dynamometer has a pair of parallel plates connected by a loop of resilient metal, with a spring disposed between the parallel plates and a dial gauge connected to measure compression of the spring when the plates are pinched together by the fingers. The free ends of the dynamometer plates have a groove defined transversely across the outer surfaces of the plates. For this type of dynamometer, the holder has a recession shaped to receive the bottom plate with the groove in the outer surface of the lower plate extending over a curved edge of the holder. A pair of set screws having slotted tips which extend between the plates of the dynamometer are used to secure the dynamometer to the holder. The lower calibration plate has an elongated, convex protrusion shaped to closely fit into the concave groove defined transversely across the outer surface of the upper dynamometer plate.

Another form of pinch grip dynamometer is the hydraulic pinch grip dynamometer, having a stem extending from a dial gauge. The free end of the stem has a push button with a concave face defined in its upper surface, and a groove defined in its lower surface. For this type of dynamometer, the holder has a cylindrical recess for receiving the dial gauge with a channel extending towards the post for receiving the stem in order to place the push button directly under the protrusion extending from the bottom surface of the lower calibration plate.

Accordingly, it is a principal object of the invention to provide a calibration stand for testing a pinch grip dynamometer.

It is another object of the invention to provide a calibration stand for field testing a pinch grip dynamometer that is portable.

It is a further object of the invention to provide a calibration stand for field testing a pinch grip dynamometer that is easily used to verify calibration of the pinch grip dynamometer with each use of the dynamometer.

Still another object of the invention is to provide a calibration stand for field testing a pinch grip dynamometer that is adaptable to a variety of different styles or shapes of pinch grip dynamometers.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
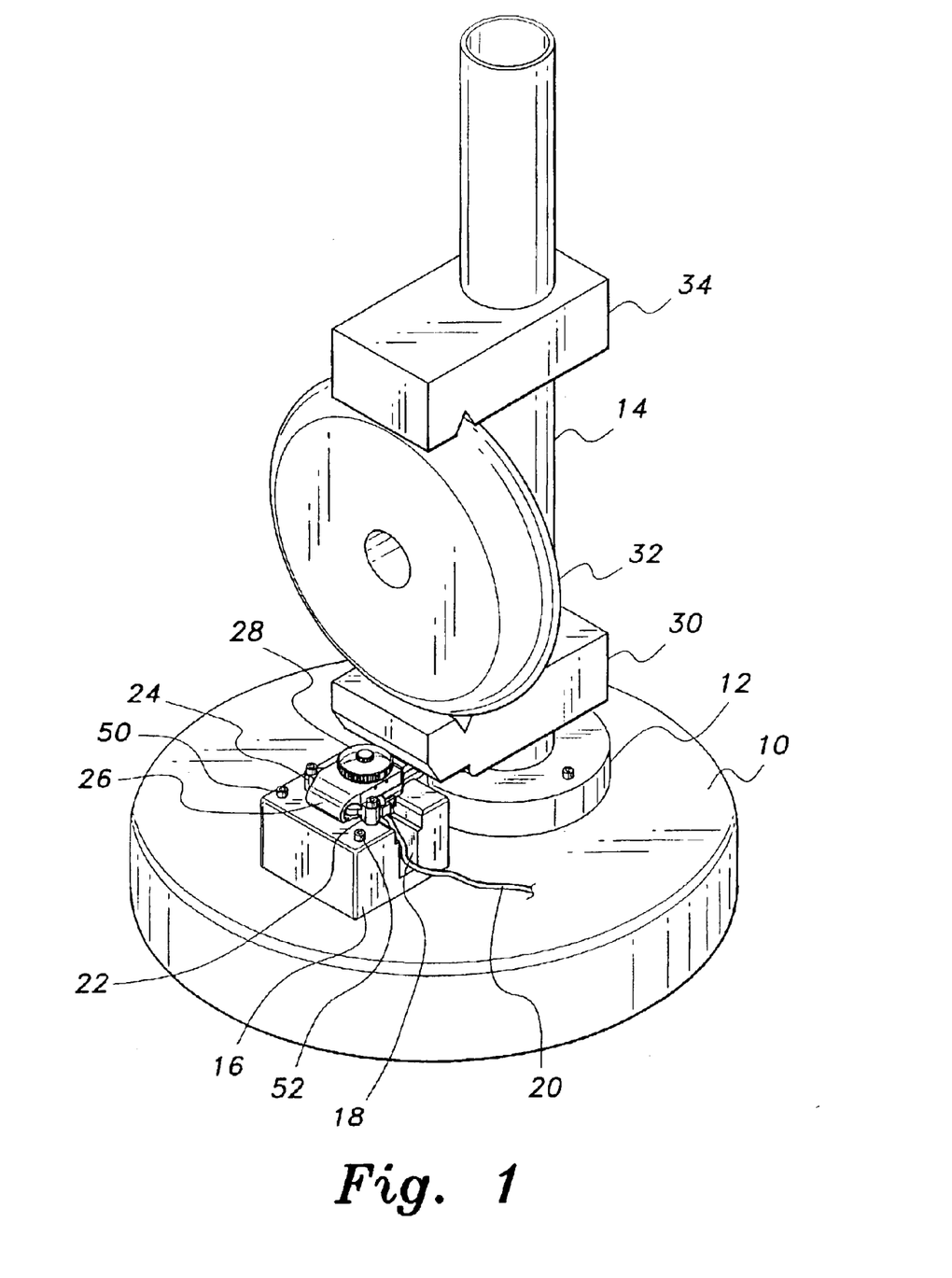
FIG. 1 is an environmental, perspective view of a pinch grip dynamometer field testing calibration stand according to the present invention with a pinch grip dynamometer and calibration weight mounted on the stand.

The present invention, as shown in FIG. 1, is a pinch grip dynamometer field testing calibration stand. The stand has a base including a platform 10, a post 14, and a mounting collar 12 for mounting the post on the platform 10. The calibration stand also includes a dynamometer holder 16 mounted on the platform 10, a lower calibration plate 30 slidable on post 14, and an upper calibration plate 34, which is also slidable on post 14. FIG. 1 shows a mechanical pinch grip dynamometer 26 mounted in the holder 16, the dynamometer being retained in the holder by clamps 22 and 24.

Figure 2:
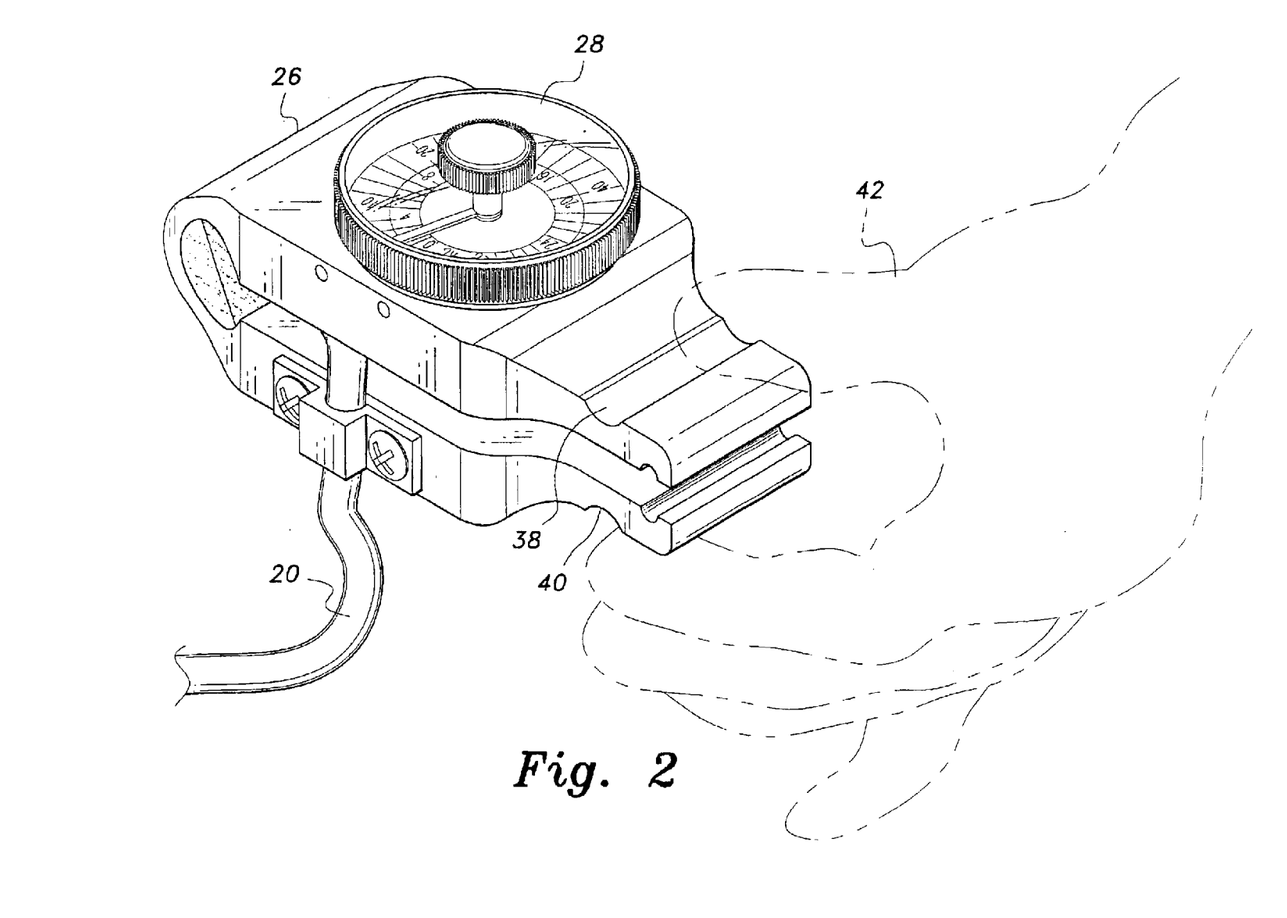
FIG. 2 is a perspective view of one kind of pinch grip dynamometer griped by the fingers of the test subject.
Figure 3:
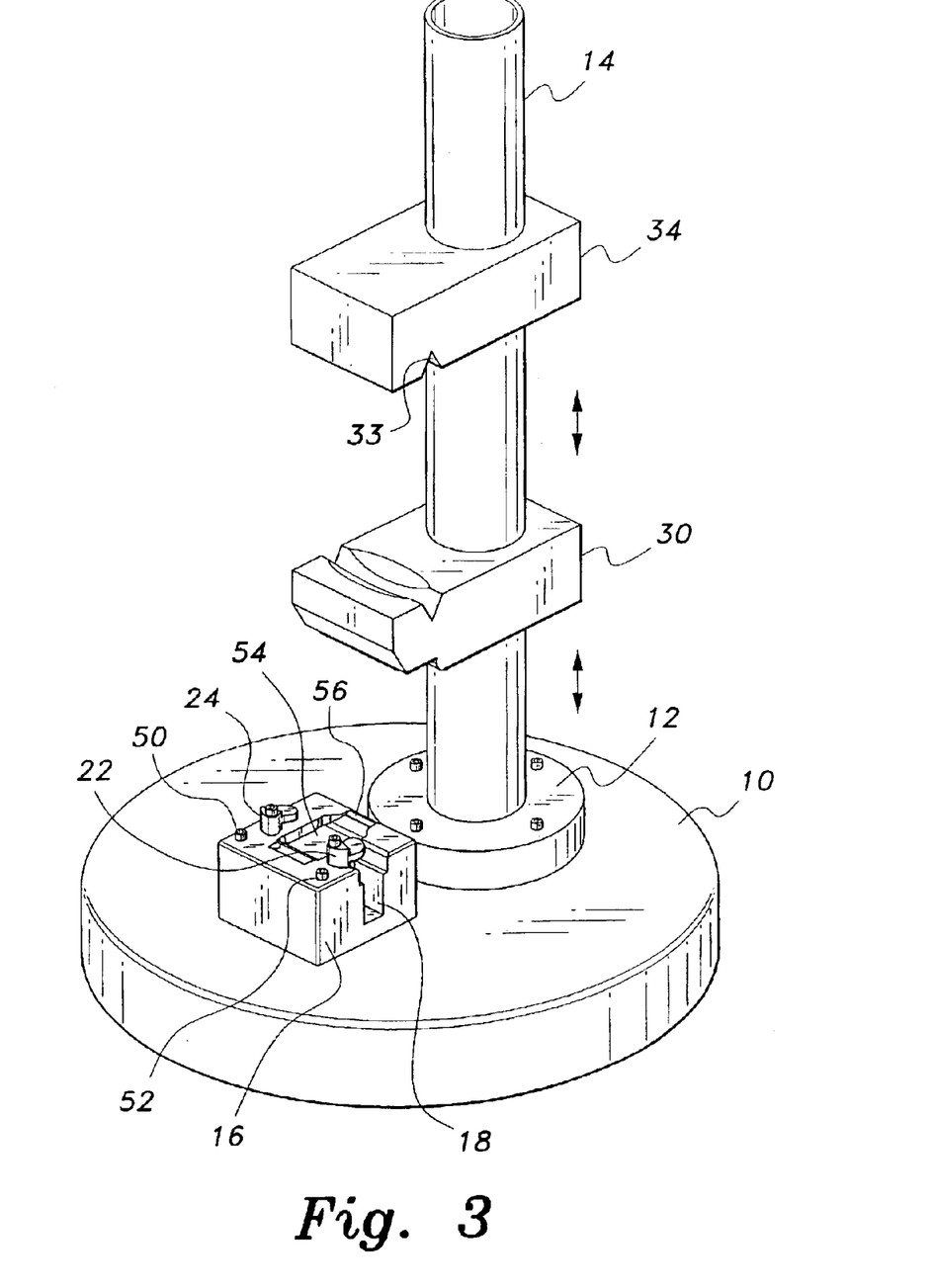
FIG. 3 is a perspective view of a pinch grip dynamometer field testing calibration stand according to the present invention.

The mechanical pinch grip dynamometer 26, which does not form a part of the present invention, is shown in use for measuring the pinch grip of a user's fingers 42 in FIG. 2. The dynamometer 26 is shown to include upper and lower plates connected by a loop. A dial gauge 28 is mounted on the upper plate, and is connected to a spring (not shown) mounted between the plates for registering compressive force applied to the plate. The dynamometer includes an electrical cable 20 which may be connected to an electrical sensor (not shown) between the dynamometer plates for measuring and recording compressive force electronically. The upper and lower dynamometer plates each have a concave groove 38 and 40, respectively, defined in their outer surfaces which are adapted for receiving the user's fingers 42. The upper groove 38 is referred to in the present application as the dynamometer's load application point.

As shown more particularly in FIGS. 3–6, the dynamometer holder 16 is removably secured to the platform 10 by a plurality of screws 50 and 52. Clamps 22 and 24 are secured to the holder 16 by screws, and each clamp 22 and 24 has a tab extending therefrom, so that the clamp screws may be loosened in order to rotate the clamps 22 and 24 to extend the tabs over the lower dynamometer plate to secure the dynamometer 26 to the holder 16, or to rotate the tabs away from the dynamometer 26 to release the dynamometer 26 from the holder 16. The holder 16 has a recess 54 defined in the top surface of the holder 16 dimensioned and configured for receiving the dynamometer 26, with a curved edge 56 facing the post 14. The curved edge 56 is dimensioned and configured in such a manner that the concave groove 40 defined in the outer surface of the lower dynamometer plate rests on and is supported by the curved edge 56 when the dynamometer 26 is properly positioned in the recess for calibration of the dynamometer 26. The holder 16 further has a slot 18 defined therein for accommodating the electrical cable 20 attached to the dynamometer 26.

Figure 4:
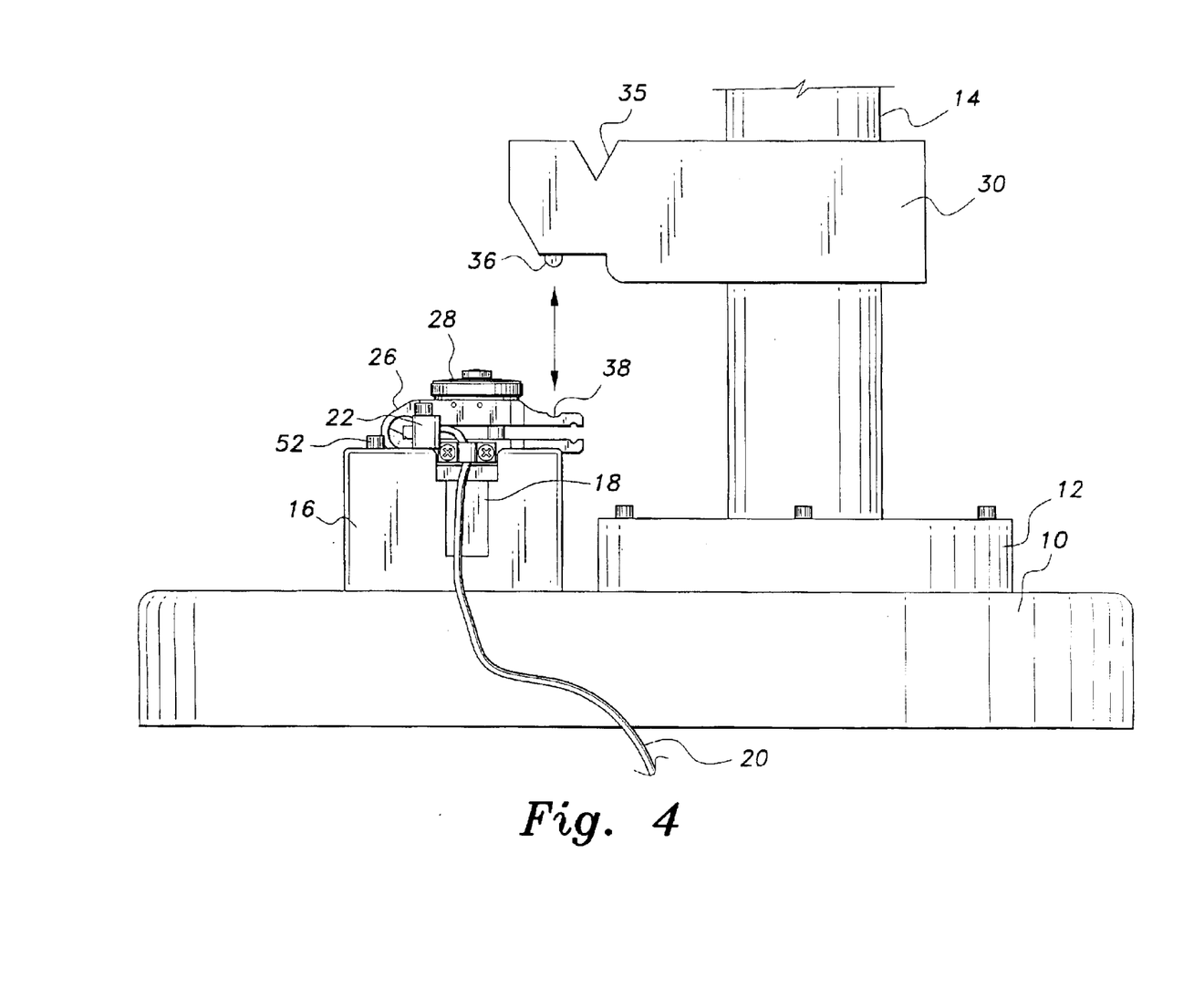
FIG. 4 is a fragmented, environmental side view of a pinch grip dynamometer field testing calibration stand showing the lower calibration plate aligned above a pinch grip dynamometer according to the present invention.
Figure 5:
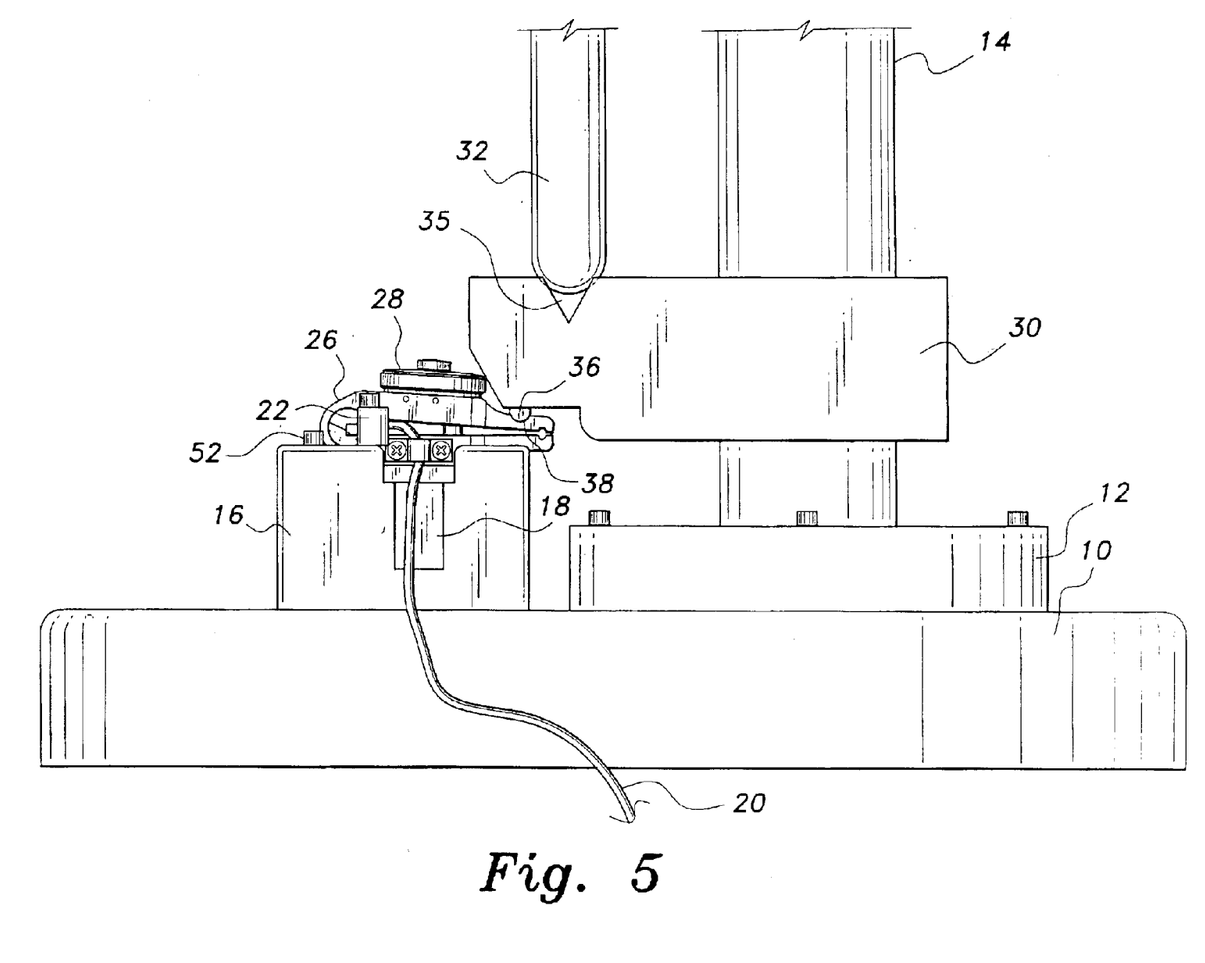
FIG. 5 is the side view of FIG. 4 with the calibration weight engaging and compressing the pinch grip dynamometer according to the present invention.
Figure 6:
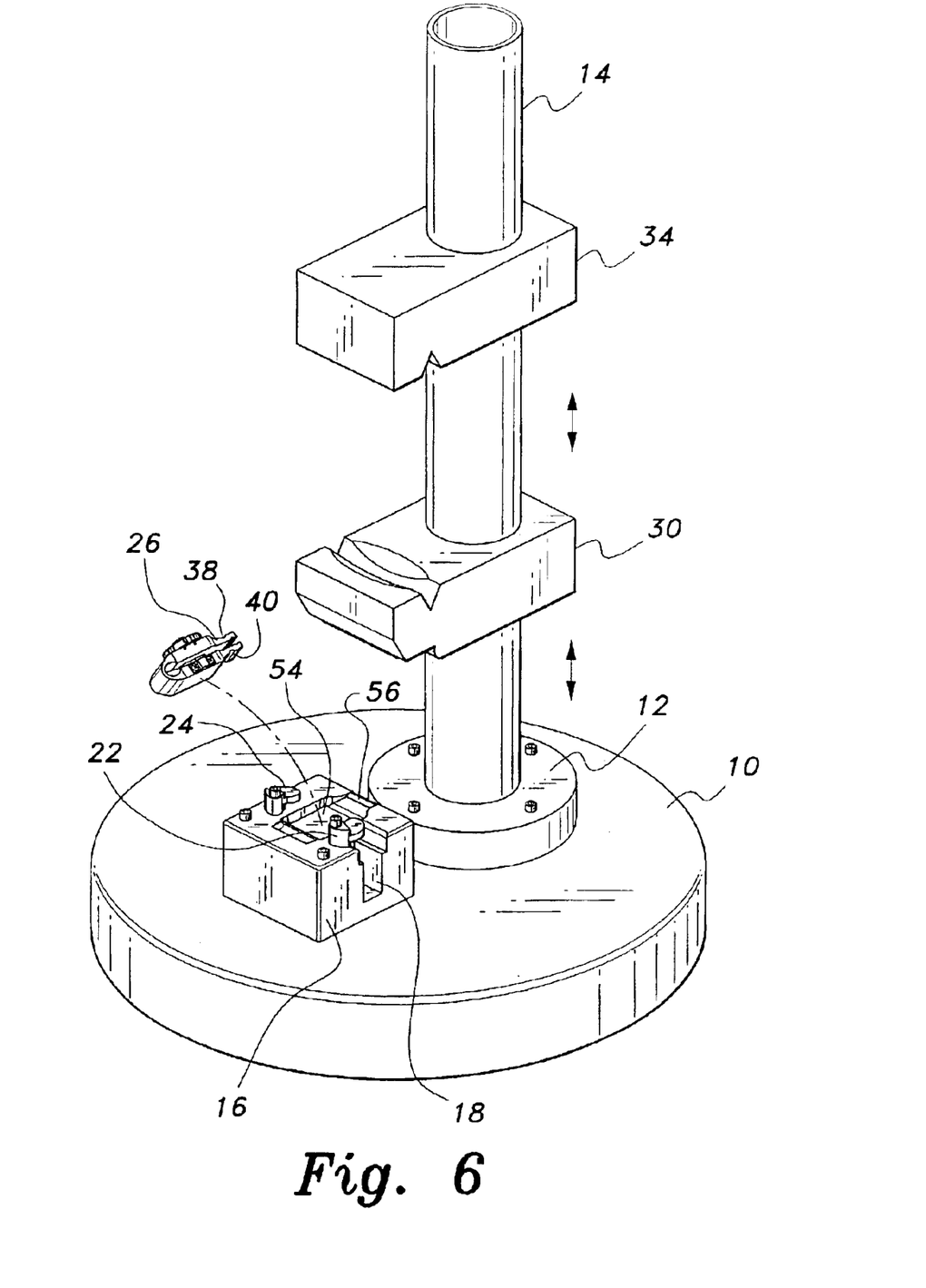
FIG. 6 is an exploded perspective view of a pinch grip dynamometer field testing calibration stand showing positioning of a pinch grip dynamometer within the holder according to the present invention.

As shown in FIGS. 4 and 5, when the dynamometer 26 is properly positioned in the holder 16, the lower calibration plate 30 is lowered on the post 14 to bear against the upper dynamometer plate. The bottom surface of the lower calibration plate 34 has a convex contact protrusion 36 depending therefrom for engaging the concave groove 38 defined in the upper dynamometer plate. In the case of a mechanical finger grip dynamometer 26 of the type shown in FIGS. 1–6, the contact protrusion 38 is an elongated convex ridge extending transversely across the bottom of lower calibration plate 30 which is machined to closely fit into concave groove 38 defined in the upper dynamometer plate so that the dynamometer plates may be squeezed at the proper point for calibration of the dynamometer 26, i.e., with lower groove 40 resting against curved edge 56 and convex protrusion 36 closely fitting and pressing into upper groove 38. With the lower calibration plate so positioned, the tare weight of the lower calibration plate 30 may be read from the dial gauge 28, or read and recorded electronically by an electrical sensor via cable 20.

The upper surface of lower calibration plate 30 has a groove 35 defined therein extending transversely across the plate 34 for receiving a calibration weight 32 of known mass. The groove 35 defined in the upper surface of the lower calibration plate 30 may be, e.g., a V-shaped groove adapted to receive an edge of standard, disk shaped calibration weight 32. The groove 35 in the lower calibration plate 30 is machined so that smaller calibration weights 32 are supported by the groove 35 in the lower calibration plate 30 without the need for further support, i.e., such calibration weights 32 are free standing in the lower calibration plate 30. For such low calibration weights 32, the force exerted by the calibration weight of known mass is determined by subtracting the dial gauge 28 reading for the lower calibration plate alone from the dial gauge 28 reading for the combined mass of the lower calibration plate 30 in combination with the calibration weight 32. Both lower calibration plate 30 and upper calibration plate 34 comprise a body having a circular or cylindrical hole extending therethrough slightly larger in diameter than post 14, so that plates 30 and 34 are slidable on post 14. Of course, the rigid body of the lower calibration plate 30 maintains the protrusion 36 and the calibrated weight 32 by known, predetermined radial distances from the post 14.

The calibration stand also includes upper calibration plate 34. Upper calibration plate 34 is used for calibration weights 32 of such mass and diameter that the calibration weight 32 is not freestanding in the groove defined in lower calibration plate 30. For this purpose, upper calibration plate 34 has a groove 33 defined in the bottom surface of the plate 34 which extends transversely across the width of upper calibration plate 34. The groove 33 defined in upper calibration plate 34 may be, e.g., an inverted V-shape. In use, the combined tare weight of the lower 30 and upper 34 calibration plates is determined by placing the lower 30 and upper plates 34 on the post without a calibration weight 32 disposed between the calibration plates 30 and 34, contact protrusion 36 resting in groove 38 and upper plate 34 resting on lower plate 30. Then upper calibration plate 34 is raised, and a calibration weight 32 of known mass is placed between the grooves 35 and 33 defined in the lower 30 and upper 34 calibration plates, respectively. The dial gauge 28 reading is obtained, and the combined tare weight of the upper 34 and lower 30 calibration plates is subtracted to obtain the force exerted by the calibrated weight 32 of known mass.

Depending upon the degree of sensitivity of the dynamometer 26 and the degree of rigor of the testing protocol required, the tare weight determination processes may be omitted and the known weights of the lower calibration plate 30 and upper calibration plate 34 may be substituted for the tare weights.

Figure 7:
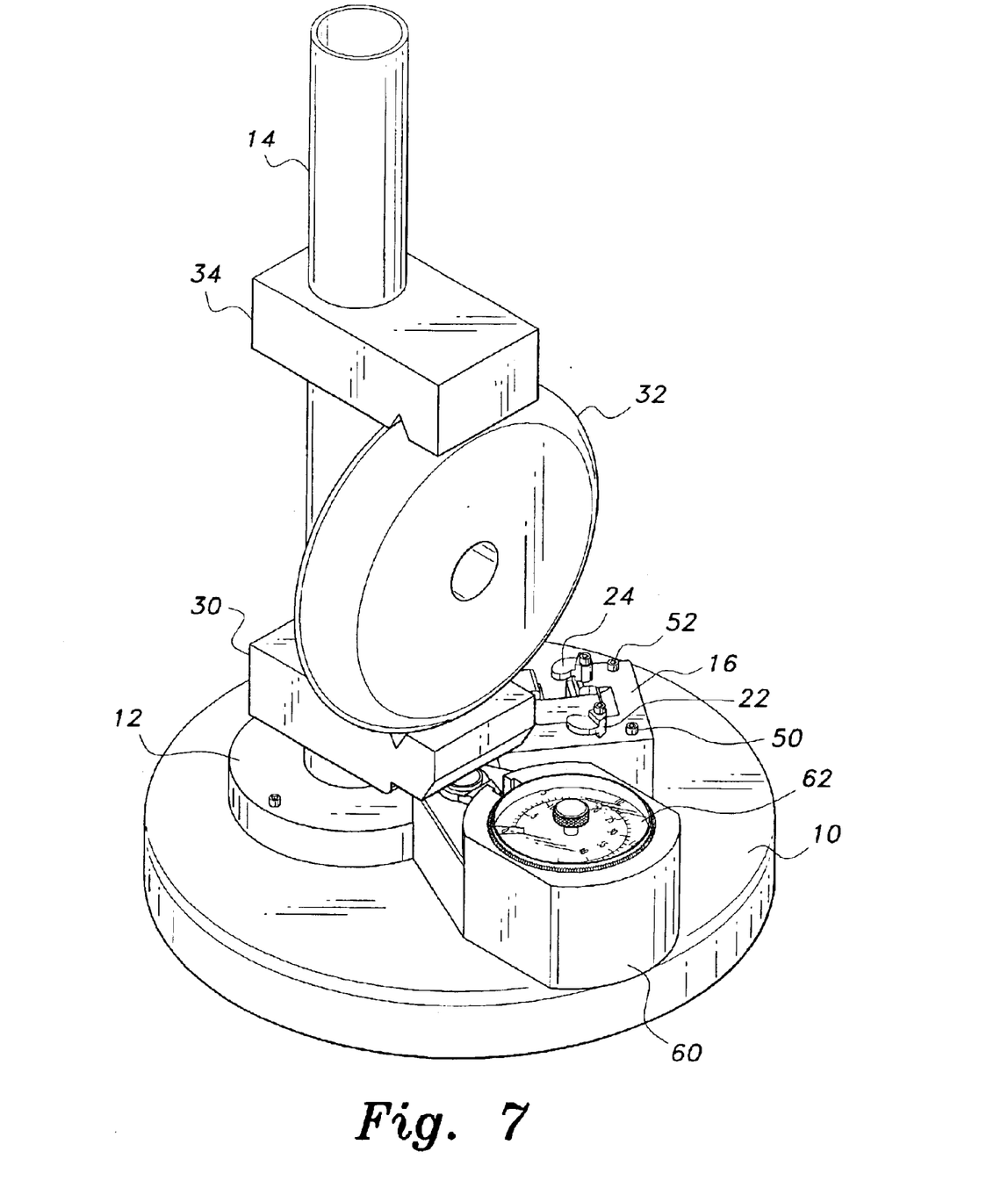
FIG. 7 is an environmental perspective view of a pinch grip dynamometer field testing calibration stand being used to calibrate a hydraulic pinch grip dynamometer, the holder for a mechanical pinch grip dynamometer resting on the base of the stand for comparison.
Figure 8:
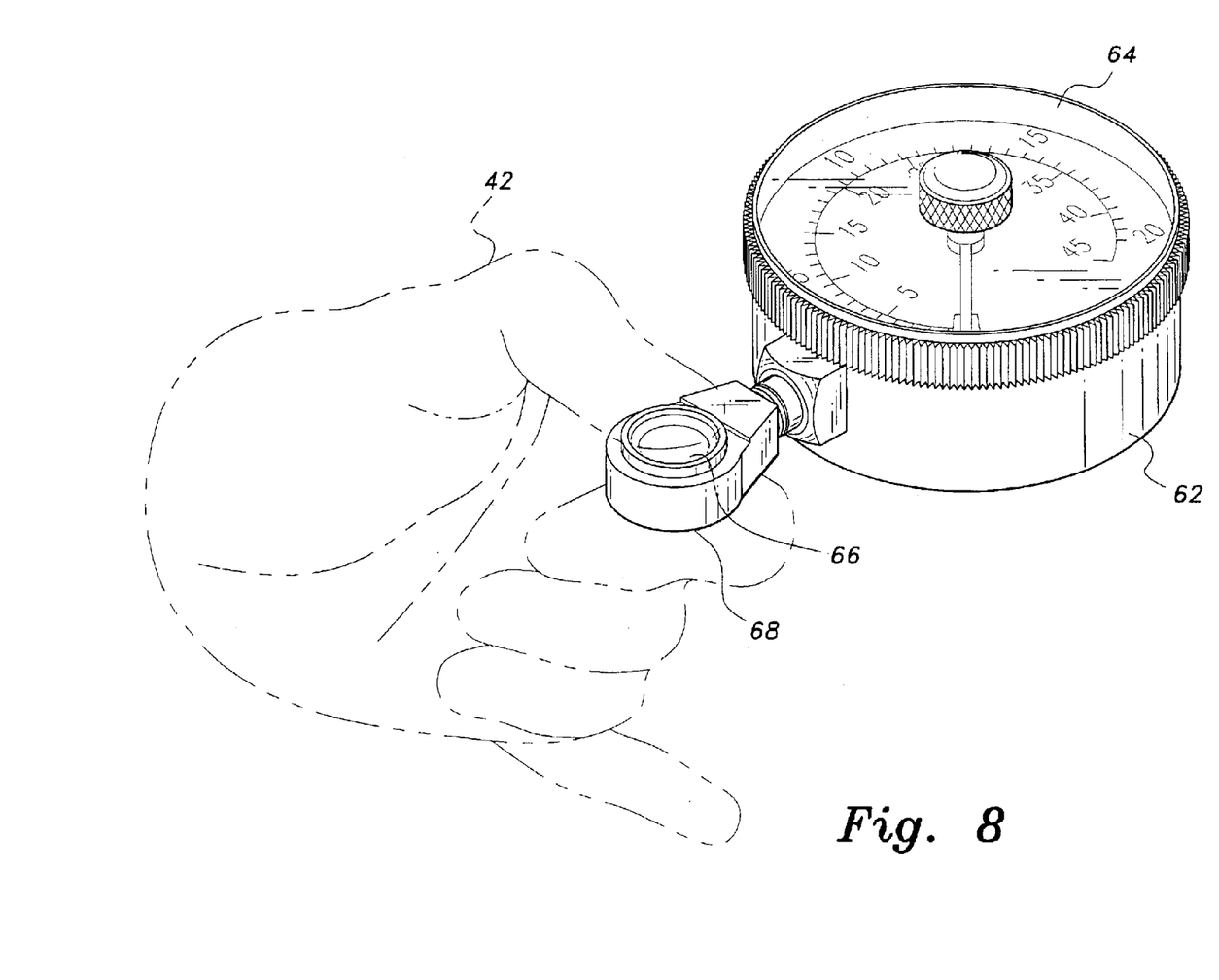
FIG. 8 is a perspective view of a hydraulic pinch grip dynamometer.

Although the pinch grip dynamometer field testing calibration stand is illustrated in FIGS. 1–6 for use with a mechanical pinch grip dynamometer 26, the principles of the calibration stand are applicable to any make or model of pinch grip dynamometer. FIG. 7 shows an alternative dynamometer holder 60 designed for use with a hydraulic pinch gauge dynamometer 62, the holder 16 for the mechanical pinch grip dynamometer 26 being shown resting on the platform 10 alongside holder 60 for comparison. FIG. 8 illustrates a conventional hydraulic pinch grip dynamometer 62, which does not form part of the present invention, but is illustrated to show operation of the present invention. The hydraulic pinch grip dynamometer includes a dial gauge 64 for indicating the force exerted by the fingers 42 of a user. The hydraulic pinch grip dynamometer 62 includes a stem 68 extending from the dial gauge 64. A push button 66 having a concave top face for receiving the tip of a user's finger 42 or thumb is mounted in the free end of the stem 68. Internally disposed in the device are a plurality of tube containing hydraulic fluid, valves, springs, etc., all connected to the dial indicator gauge 64 to indicate hydraulic force applied when the user pinches down on the push button 66. The push button 66 is referred to in the present application as the dynamometer's load application point.

Figure 10:
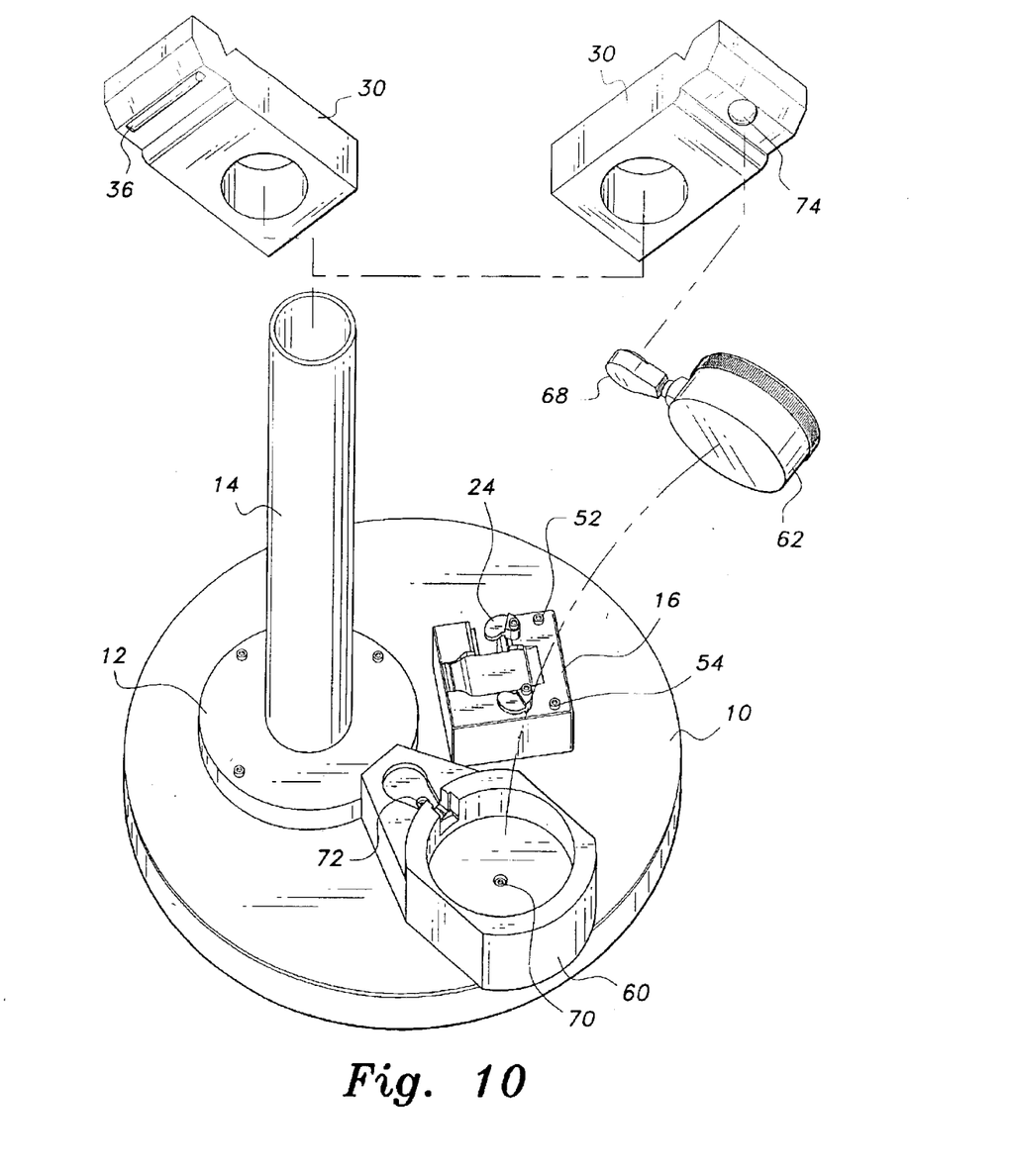
FIG. 10 is an exploded perspective view of the pinch grip dynamometer field testing calibration stand showing the style of pinch grip dynamometer, two alternative dynamometer holders, and two alternative lower calibration plates according to the present invention.

As shown particularly in FIGS. 7 and 10, the holder 60 for the hydraulic pinch grip dynamometer 62 has a recess 70 which is shaped in the form of a cylindrical well for receiving dial indicator gauge 64, and a generally channel shaped recess 72 extending from the cylindrical recess 70 towards the post 14. The holder 60 is secured to the platform 10 by screws. As shown in FIG. 7, the hydraulic pinch grip dynamometer is retained in the holder 60 by the close machining of the recesses 70 and 72. It will be noted that the front face of the holder 16 abuts the collar 12 in order to properly align the push button 66 under the protrusion on the bottom surface of lower calibration plate 30, as described below.

Figure 9:
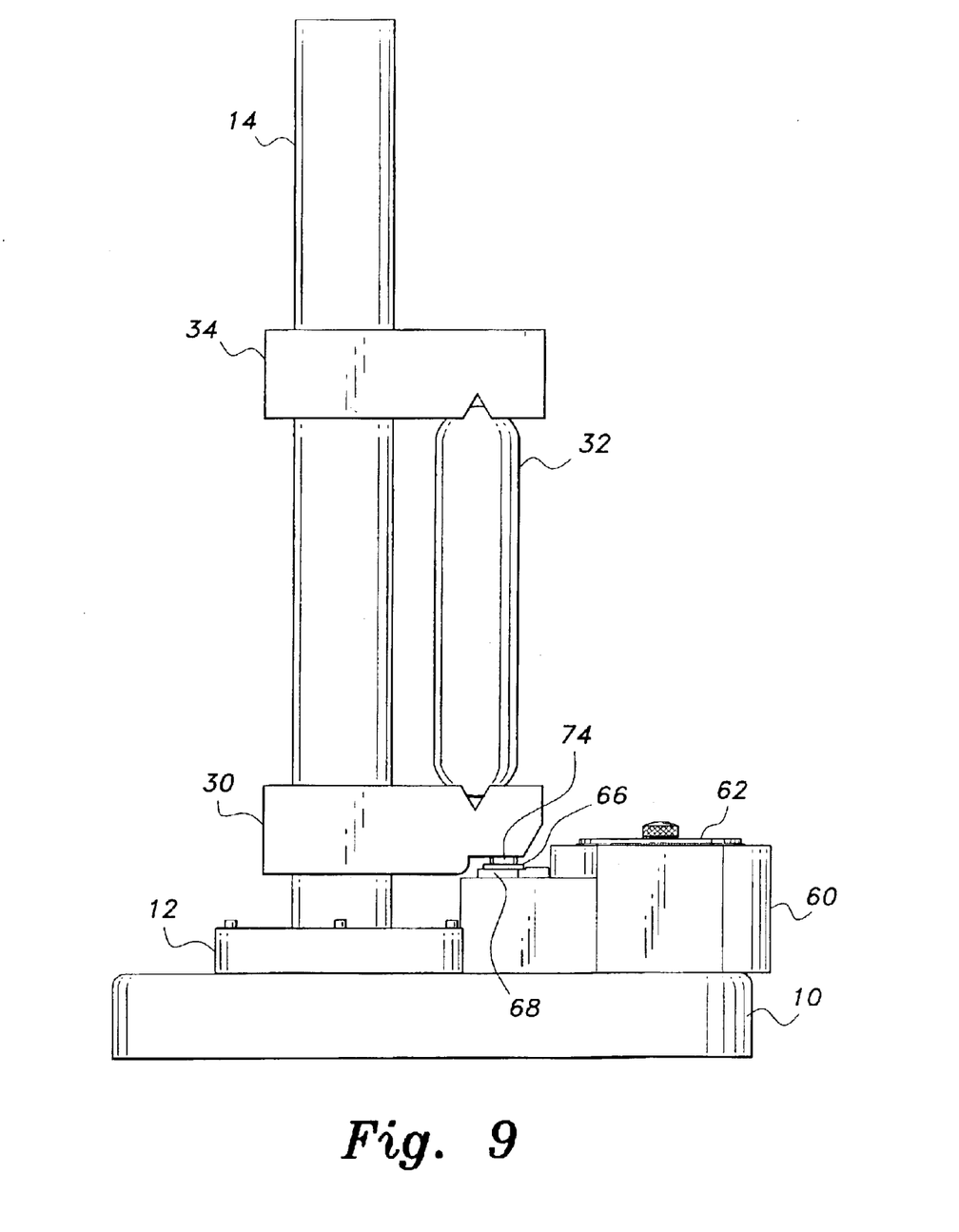
FIG. 9 is an environmental side view of a pinch grip dynamometer field testing calibration stand adapted to calibrate a hydraulic pinch grip dynamometer according to the present invention.

As shown in FIG. 10, the protrusion on the bottom face of the lower calibration plate 30 may also be modified for use in calibrating the hydraulic pinch grip dynamometer 62. As shown in the upper right corner of FIG. 10, a lower calibration plate 30 used for calibrating a hydraulic pinch grip dynamometer 62 has a convex protrusion 74 which is ball shaped or bubble shaped to closely fit the concave recess in the top face of the push button 66. As shown in FIG. 9, in use the hydraulic pinch grip dynamometer 62 is placed in holder 60 to align push button 66 with the convex protrusion 74 on the bottom surface of lower calibration plate 30, which is lowered on post 12 to contact push button 66, and the tare weight of the lower calibration plate 30 is read from the dial indicator 64 and recorded. A calibrated weight 32 of known mass is then placed in the groove 35 defined in lower calibration plate 30, and the force exerted by calibrated weight 32 is calculated by subtracting the tare weight from the combined reading, as described above for the mechanical pinch grip dynamometer 26. The upper end of the calibrated weight 32 may be supported by upper calibration plate 34, if necessary, as described above.

As shown in FIG. 10, the pinch grip dynamometer field testing calibration stand may be marketed in the form of a kit. For this purpose, a holder 16 for a mechanical pinch grip dynamometer 26 and a holder 60 for a hydraulic pinch grip dynamometer 62 may each be attached to the platform 10 at different radial positions from the post 14. Alternatively, since both holders 16 and 60 are attached to the platform 10 by screws, one holder may be attached to the platform at a time, the holders 16 and 60 being interchangeably attached to the same position on the platform. The kit may include two lower calibration plates 30, one having an elongated convex protrusion 36 for use with calibrating mechanical dynamometers, and one having a ball or bubble shaped convex protrusion 74 for calibrating hydraulic dynamometers. The kit would also include an upper calibration plate 34 for supporting calibration weights 32, as needed.

It will be seen that the pinch grip dynamometer field testing calibration stand of the present invention provides a much needed, compact, portable, and economic solution to the problem of providing accurate, precise, reliable and repeatable measurements of pinch grip strength.

It is to be understood that the present invention is not limited to the embodiments described above, but encompasses any and all embodiments within the scope of the following claims.

We claim:

1. A pinch grip dynamometer field testing calibration stand comprising:

a platform;

a mounting collar attached to said platform;

a vertical post mounted in said mounting collar on said platform;

wherein said mounting collar is disposed around a lower end of said vertical post;

a dynamometer holder attached to said platform, the holder being a rigid body having a top surface and a recess defined in the top surface adapted for holding a pinch grip dynamometer with the dynamometer's load application point located a fixed distance from said post; and a lower calibration plate slidable on said post, the lower calibration plate being a rigid body having a top surface and a bottom surface, the top surface being adapted for supporting a calibration mass of known weight, and the bottom surface being adapted for applying a load to the dynamometer's load application point.

2. The pinch grip dynamometer field testing calibration stand according to claim 1, wherein the bottom surface of said lower calibration plate has a convex protrusion extending therefrom adapted for applying a load to a concave surface defining the dynamometers load application point.

3. The pinch grip dynamometer field testing calibration stand according to claim 2, wherein said convex protrusion comprises an elongated convex ridge extending across the bottom surface of said lower calibration plate adapted for closely fitting a concave groove defined in an upper plate of a mechanical pinch grip dynamometer.

4. The pinch grip dynamometer field testing calibration stand according to claim 2, wherein said convex protrusion comprises a ball shaped protrusion adapted for closely fitting a concave recess defined in a push button load application point of a hydraulic pinch grip dynamometer.

5. The pinch grip dynamometer field testing calibration stand according to claim 1, wherein the groove is V-shaped in cross section.

6. The pinch grip dynamometer field testing calibration stand according to claim 1, further comprising an upper calibration plate, the upper calibration plate being a rigid body having a bottom surface, the bottom surface having an elongated groove defined therein adapted for supporting an upper portion of the calibrated weight of known mass.

7. The pinch grip dynamometer field testing calibration stand according to claim 1, wherein the recess defined in said dynamometer holder comprises a substantially rectangular recess adapted for receiving a bottom plate of a mechanical pinch grip dynamometer, the recess having a curved edge facing said post adapted for closely fitting and supporting a groove defined in the bottom plate of the mechanical pinch grip dynamometer.

8. The pinch grip dynamometer field testing calibration stand according to claim 1, further comprising a first clamp and a second clamp attached to said dynamometer holder on opposite sides of the rectangular recess, each clamp comprising a body having a clamp screw extending therethrough and a tab extending therefrom, the tab being adapted for insertion between the bottom plate and a parallel top plate of the mechanical pinch grip dynamometer.

9. The pinch grip dynamometer field testing calibration stand according to claim 1, wherein the recess defined in said dynamometer holder comprises:

a cylindrical recess adapted for receiving a dial indicator gauge of a hydraulic pinch grip dynamometer; and a channel extending from the cylindrical recess towards said post, the channel being adapted for receiving a stem of the hydraulic pinch grip dynamometer.

10. The pinch grip dynamometer field testing calibration stand according to claim 1, wherein said dynamometer holder further comprises:

a first dynamometer holder adapted for receiving a mechanical pinch grip dynamometer; and a second dynamometer holder adapted for receiving a hydraulic pinch grip dynamometer, said first and second dynamometer holders being attached to said platform and spaced apart radially from said post.

11. The pinch grip dynamometer field testing calibration stand according to claim 1, wherein said dynamometer holder further comprises:

a first dynamometer holder adapted for receiving a mechanical pinch grip dynamometer; and a second dynamometer holder adapted for receiving a hydraulic pinch grip dynamometer, said first and second dynamometer holders being interchangeably attached to said platform at a common location.

* * * * *